United States Patent [19]

Gries et al.

[11] Patent Number: 5,196,579
[45] Date of Patent: Mar. 23, 1993

[54] PROCESS FOR THE RECOVERY OF PERFLUOROETHERCARBOXYLIC ACIDS

[75] Inventors: Thomas Gries, Frankfurt am Main; Klaus-Dieter Ginzel, Hofheim am Taunus; Frank Ebmeyer, Frankfurt am Main, all of Fed. Rep. of Germany

[73] Assignee: Hoechst AG, Frankfurt am Main, Fed. Rep. of Germany

[21] Appl. No.: 806,497

[22] Filed: Dec. 13, 1991

[30] Foreign Application Priority Data

Dec. 24, 1990 [DE] Fed. Rep. of Germany ....... 4041718

[51] Int. Cl.$^5$ ...................... C07C 51/42; C07C 59/00; C07C 17/38
[52] U.S. Cl. ................................... 562/580; 562/586; 570/262; 570/263
[58] Field of Search ................ 562/580, 586; 570/262, 570/263

[56] References Cited

FOREIGN PATENT DOCUMENTS

| | | | |
|---|---|---|---|
| 0707361 | 4/1965 | Canada ................................. | 562/586 |
| 3828848 | 3/1990 | Fed. Rep. of Germany . | |
| 3902803 | 8/1990 | Fed. Rep. of Germany . | |
| 58-103334 | 6/1983 | Japan . | |
| 0971369 | 9/1964 | United Kingdom ................ | 562/586 |

*Primary Examiner*—José G. Dees
*Assistant Examiner*—Porfirio Nazaro
*Attorney, Agent, or Firm*—Connolly & Hutz

[57] ABSTRACT

The invention relates to a process for the recovery of perfluoroethercarboxylic acids from the crude product of the electrochemical conversion of these acids or of one of their soluble salts to perfluorinated ethers, in which the perfluoroethercarboxylic acids and their esters contained in the crude product are separated off with the aid of a solid basic alkali metal salt or its solution and converted, by reaction of the resulting salts with a strong acid, to the corresponding perfluoroethercarboxylic acids.

6 Claims, No Drawings

PROCESS FOR THE RECOVERY OF PERFLUOROETHERCARBOXYLIC ACIDS

The invention relates to a process for the recovery of perfluoroethercarboxylic acids from contaminants occurring in the crude product during the electrochemical conversion of perfluoroethercarboxylic acids to perfluorinated ethers.

The recovered perfluoroethercarboxylic acids can be reused for the synthesis of perfluorinated ethers. The yield of the synthesis is thereby increased and the amount of waste reduced.

The preparation of perfluorinated ethers is accomplished in good yields by Kolbe electrolysis of perfluorinated ethercarboxylic acids or their soluble salts (JP-58/103 334, DE-A 3 828 848):

$$2R_f\text{—COOH} \rightarrow R_f\text{—}R_f + 2CO_2 + H_2$$

in which $$R_f = C_aF_{2a+1}O\text{—}(C_3F_6O)_m\text{—}CF(CF_3)\text{—}$$

where a = 1, 2 or 3
and m = 0, 1, 2 or 3.

The perfluoroethercarboxylic acids used in this electrolysis are prepared by oligomerization of hexafluoropropylene epoxide (HFPO) to give carboxylic acid fluorides and their hydrolysis to give perfluoroethercarboxylic acids:

nHFPO $\longrightarrow$ $$C_3F_7O\text{—}(CF(CF_3)\text{—}CF_2\text{—}O)_{n-2}\text{—}CF(CF_3)\text{—}COF \xrightarrow{H_2O}$$

$$C_3F_7O\text{—}(CF(CF_3)\text{—}CF_2\text{—}O)_{n-2}\text{—}CF(CF_3)\text{—}COOH$$

The perfluoroethercarboxylic acids thus formed are subsequently separated by distillation. However, even after the distillation, such a perfluoroethercarboxylic acid can still be contaminated by the next higher or next lower homolog or by both, although their proportion is generally less than 5% by weight. If a mixture of two carboxylic acids $R_f$—COOH and $R_f'$—COOH, or their salts is electrolyzed, a mixture of perfluoroethers $R_f$—$R_f$, $R_f'$—$R_f'$ and $R_f$—$R_f'$ is obtained. The same is true if three carboxylic acids are present in the mixture.

The perfluoroethers prepared by electrolysis of the perfluoroethercarboxylic acids contain as contaminants inter alia unconverted perfluoroethercarboxylic acids and their esters resulting from reaction of the carboxylic acids with the solvent used for the electrolysis (an alcohol or an alcohol-water mixture). Suitable alcohols for this are for example methanol, ethanol, propanol, butanol, pentanol, glycol, diethylene glycol and triethylene glycol, in particular methanol and ethanol.

A process for the complete removal of the contaminants by thermal decomposition to substances that are no longer utilizable is described in DE-A 3 902 803. However, as the contaminants comprise to a large extent valuable perfluorinated material, it is desirable to recover this as far as possible and to reuse it in the synthesis of perfluorinated ethers.

The invention accordingly relates to a process for the recovery of perfluoroethercarboxylic acids of the formula I $$R_f\text{—COOH}, \tag{I}$$

in which $R_f = C_aF_{2a+1}O\text{—}(C_3F_6O)_m\text{—}CF(CF_3)\text{—}$
where a = 1, 2 or 3
and m = 0, 1, 2 or 3 from the crude product of the electrochemical preparation of perfluorinated ethers, which comprises separating off the perfluoroethercarboxylic acid of the formula I and its ester of the formula II $$R_f\text{—COOR}, \tag{II}$$

in which $R_f$ is as defined under (I) and
$R = \text{—}C_cH_{2c+1}$ where c = 1, 2, 3, 4 or 5 or
$R = \text{—}C_dH_{2d+1}O_e$ where d = 2, 3, 4, 5 or 6 and e = 1, 2 or 3 which are contained in the crude product, with the aid of a solid basic alkali metal salt or its solution, and reacting the resulting salts with a strong acid for conversion into the corresponding perfluoroethercarboxylic acid of the formula I.

Two perfluoroethercarboxylic acids may be recovered in the same way from the crude product of the electrochemical conversion of a mixture of these acids. The invention therefore also relates to a process for the recovery of the two perfluoroethercarboxylic acids of the formulae I and I'

$$R_f\text{—COOH}, \tag{I}$$

in which
$R_f = C_aF_{2a+1}O\text{—}(C_3F_6O)_m\text{—}CF(CF_3)\text{—}$
where a = 1, 2 or 3 and m = 0, 1, 2 or 3

$$R_f'\text{—COOH}, \tag{I'}$$

in which
$R_f' = C_bF_{2b+1}O\text{—}(C_3F_6O)_n\text{—}CF(CF_3)\text{—}$
where b = 1, 2 or 3 and n = 0, 1, 2 or 3 from the crude product of the electrochemical conversion of these acids or their soluble salts to perfluorinated ethers, which comprises separating off the perfluoroethercarboxylic acids of the formulae I and I' and their esters of the formulae II and II'

$$R_f\text{—COOR} \tag{II}$$

$$R_f'\text{—COOR} \tag{II'}$$

in which $R_f$ and $R_f'$ are as defined under (I) and (I')
and $R = \text{—}C_cH_{2c+1}$ where c = 1, 2, 3, 4 or 5
or $R = \text{—}C_dH_{2d+1}O_e$ where d = 2, 3, 4, 5 or 6 and e = 1, 2 or 3 which are contained in the crude product, with the aid of a solid basic alkali metal salt or its solution, and reacting the resulting salts with a strong acid for conversion into the corresponding perfluoroethercarboxylic acids of the formulae I and I'.

If only one perfluoroethercarboxylic acid was electrolyzed, this may be recovered in the same way. The invention accordingly further relates to a process for the recovery of a perfluoroethercarboxylic acid of the formula I $$R_f\text{—COOH}, \tag{I}$$

in which
$R_f = C_aF_{2a+1}O-(C_3F_6O)_m-CF(CF_3)-$
where a = 1, 2 or 3
and m = 0, 1, 2 or 3
from the crude product of the electrochemical conversion of this acid or one of its soluble salts to a perfluorinated ether, which comprises separating off the perfluoroethercarboxylic acid of the formula I and its ester of the formula II $$R_f-COOR, \qquad (II)$$

in which
$R_f$ is as defined under (I) and
$R = -C_cH_{2c+1}$ where c = 1, 2, 3, 4 or 5 or
$R = -C_dH_{2d+1}O_e$ where d = 2, 3, 4, 5 or 6 and e = 1, 2 or 3
which are contained in the crude product, with the aid of a solid basic alkali metal salt or its solution, and reacting the resulting salt with a strong acid for conversion into the corresponding perfluoroethercarboxylic acid of the formula I.

The separation of the perfluoroethercarboxylic acids and the esters can be accomplished by liquid-liquid extraction using basic alkali metal salt solutions, or with the aid of solid basic alkali metal salts, e.g. by percolation of the crude product over a fixed bed of the hydroxide or carbonate of an alkali metal. Preferably, basic Na or K salts and/or their solutions are used, particularly the hydroxides or carbonates of Na or K. Generally, the alkali metal salts are used in a 1 to 5 fold excess. The concentration of the alkali metal salt solutions is generally 5–50% by weight, preferably 15–25% by weight.

Extraction of the perfluoroether crude products with an aqueous solution of basic alkali metal salts and simple phase separation of the extract gives a concentrated salt-containing aqueous phase, and also a heavier perfluoroether phase and a lighter aqueous phase. The salt-containing aqueous phase mentioned contains, in addition to the salts of the perfluorinated ethercarboxylic acids, excess basic alkali metal salts, and, in emulsified form, a small fraction of the perfluoroether (less than 1% by weight), the majority of this being in the perfluoroether phase. If the salt-containing aqueous phase is reacted with a strong acid, e.g. aqueous sulfuric acid, at room temperature, two phases result. The heavy phase contains the desired perfluoroethercarboxylic acids and the said fraction, emulsified in the salt-containing aqueous phase, of perfluorinated ethers. An advantageous effect results from the low content of water and of fluoride ions, so that the heavy phase may be used without further purification for the electrochemical preparation of perfluorinated ethers, as described in JP-58/103 334 or in DE-A 3 828 848. Suitable acids are for example sulfuric acid and hydrohalic acids, preferably sulfuric acid, hydrochloric acid and hydrobromic acid, particularly 10–30% strength sulfuric acid.

The process according to the invention increases the yield of the perfluoroether synthesis and decreases the quantity of waste materials.

EXAMPLES

The percentage figures given below are percentages by weight throughout.

EXAMPLE 1

6.1 kg of crude product from the electrochemical synthesis of $(C_3F_7-O-CF(CF_3)-)_2$, containing 0.4% of the unconverted acid $C_3F_7-O-CF(CF_3)-COOH$ and 1.6% of the methyl ester $C_3F_7-O-CF(CF_3)-COOCH_3$, were mixed with 366 g of 20% strength potassium hydroxide solution in a glass stirred apparatus. After phase separation, the middle phase obtained comprised 242 g of an alkaline solution of the following composition:
56% of $C_3F_7-O-CF(CF_3)-COOK$
23% of $(C_3F_7-O-CF(CF_3)-)_2$
21% of aqueous potassium hydroxide solution
230 g of this solution were introduced into a 1 l glass flask fitted with a magnetic stirrer and a dropping funnel, at 20° C. in a water bath, and 276 g of 20% strength sulfuric acid were added in the course of 20 min with vigorous stirring. After addition was completed, the resulting phases were separated. The heavy phase (167 g) contained
65% $C_3F_7-O-CF(CF_3)-COOH$
32% $(C_3F_7-O-CF(CF_3)-)_2$
3% water and
14 mg/l of fluoride.
The light phase (330 g) contained aqueous sulfuric acid and 170 mg/l of fluoride.

EXAMPLE 2

16.6 kg of a perfluoroether crude product prepared by Kolbe electrolysis and containing
94% of $(C_3F_7-O-CF(CF_3)-CF_2-O-CF(CF_3)-)_2$,
4.1% of $C_3F_7-O-CF(CF_3)-CF_2-O-CF(CF_3)-COOCH_3$ and
1.9% of $C_3F_7-O-CF(CF_3)-CF_2-O-CF(CF_3)-COOH$,
were extracted with 1.6 kg of an 18% strength aqueous potassium hydroxide solution. Phase separation gave 1584 g of a salt solution of the following composition as the middle phase:
68% of $C_3F_7-O-CF(CF_3)-CF_2-O-CF(CF_3)-COOK$
21% of $(C_3F_7-O-CF(CF_3)-CF_2-O-CF(CF_3)-)_2$
11% of aqueous potassium hydroxide solution.
After reaction with 1100 g of 25% strength aqueous sulfuric acid, 1340 g of perfluoroethercarboxylic acid solution of the following composition were separated off as the heavy phase:
73.1% of $C_3F_7-O-CF(CF_3)-CF_2-O-CF(CF_3)-COOH$
24.7% of $(C_3F_7-O-CF(CF_3)-CF_2-O-CF(CF_3)-)_2$
2.2% of water
5.0 mg/l of fluoride.
The light phase (1330 g) contained aqueous sulfuric acid and 100 mg/l of fluoride.

We claim:
1. A process for the recovery of perfluoroethercarboxylic acids of the formula I

$$R_f-COOH, \qquad (I)$$

in which
$R_f = C_aF_{2a+1}O-(C_3F_6O)_m-CF(CF_3)-$
where a = 1, 2 or 3
and m = 0, 1, 2 or 3
from the crude product of the electrochemical preparation of perfluorinated ethers, which comprises separating off the perfluoroethercarboxylic acid of the formula I and its ester of the formula II $$R_f\text{—COOR},$$

in which
$R_f$ is as defined under (I) and
$R = -C_cH_{2c+1}$ where $c = 1, 2, 3, 4$ or $5$ or
$R = -C_dH_{2d+1}O_e$ where $d = 2, 3, 4, 5$ or $6$ and $e = 1, 2$ or $3$
which are contained in the crude product, with the aid of a solid basic alkali metal salt or its solution, and reacting the resulting salts with a strong acid for conversion into the corresponding perfluoroethercarboxylic acid of the formula I.

2. The process as claimed in claim 1, wherein the alkali metal salt used is the hydroxide or carbonate of sodium or potassium.

3. A process for the recovery of the two perfluoroethercarboxylic acids of the formulae I and I'

$$R_f\text{—COOH}, \qquad (I)$$

in which
$R_f = C_aF_{2a+1}O\text{—}(C_3F_6O)_m\text{—CF(CF}_3)\text{—}$
where $a = 1, 2$ or $3$ and $m = 0, 1, 2$ or $3$ $$R_f'\text{—COOH}, \qquad (I')$$

in which
$R_f' = C_bF_{2b+1}O\text{—}(C_3F_6O)_n\text{—CF(CF}_3)\text{—}$
where $b = 1, 2$ or $3$ and $n = 0, 1, 2$ or $3$
from the crude product of the electrochemical conversion of these acids or their soluble salts to perfluorinated ethers, which comprises separating off the perfluorethercarboxylic acid of the formulae I and I' and their esters of the formulae II and II'

$$R_f\text{—COOR} \qquad (II)$$

$$R_f'\text{—COOR} \qquad (II')$$

in which $R_f$ and $R_f'$ are as defined under (I) and (I')
and $R = -C_cH_{2c+1}$ where $c = 1, 2, 3, 4$ or $5$ or
$R = -C_dH_{2d+1}O_e$ where $d = 2, 3, 4, 5$ or $6$ and $e = 1, 2$ or $3$
which are contained in the crude product, with the aid of a solid basic alkali metal salt or its solution, and reacting the resulting salts with a strong acid for conversion into the corresponding perfluoroethercarboxylic acids of the formulae I and I'.

4. The process as claimed in claim 3, wherein the alkali metal salt used is the hydroxide or carbonate of sodium or potassium.

5. A process for the recovery of a perfluoroethercarboxylic acid of the formula I $$R_f\text{—COOH}, \qquad (I)$$

in which
$R_f = C_aF_{2a+1}O\text{—}(C_3F_6O)_m\text{—CF(CF}_3)\text{—}$
where $a = 1, 2$ or $3$
and $m = 0, 1, 2$ or $3$
from the crude product of the electrochemical conversion of this acid or one of its soluble salts to a perfluorinated ether, which comprises separating off the perfluoroethercarboxylic acid of the formula I and its ester of the formula II $$R_f\text{—COOR}, \qquad (II)$$

in which
$R_f$ is as defined under (I) and
$R = -C_cH_{2c+1}$ where $c = 1, 2, 3, 4$ or $5$ or
$R = -C_dH_{2d+1}O_e$ where $d = 2, 3, 4, 5$ or $6$ and $e = 1, 2$ or $3$
which are contained in the crude product, with the aid of a solid basic alkali metal salt or its solution, and reacting the resulting salt with a strong acid for conversion into the corresponding perfluoroethercarboxylic acid of the formula I.

6. The process as claimed in claim 5, wherein the alkali metal salt used is the hydroxide or carbonate of sodium or potassium.

* * * * *